US006274138B1

(12) United States Patent
Bandman et al.

(10) Patent No.: US 6,274,138 B1
(45) Date of Patent: Aug. 14, 2001

(54) HUMAN MITOCHONDRIAL MALATE DEHYDROGENASE

(75) Inventors: Olga Bandman; Neil C. Corley, both of Mountain View; Purvi Shah, Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 08/922,957

(22) Filed: Sep. 3, 1997

(51) Int. Cl.$^7$ ..................................................... A61K 38/44
(52) U.S. Cl. ............................ 424/94.4; 435/26; 435/189
(58) Field of Search ...................... 435/189, 26; 424/94.4

(56) References Cited

PUBLICATIONS

Swissprot Accession P40926 (Rel 31) "Malate Dehydrogenase, Mitochondrial Precursor" (Human) Amino acid residues 1–109 disclosed on Feb. 1, 1995.*
Swissprot Accession P40926 (Rel 39) "Malate Dehydrogenase, Mitochondrial Precursor" (Human) Amino acid residues 1–338 disclosed on Feb. 15, 2000.*
Swissprot Accession P08249 (Rel 11) "Malate Dehydrogenase, Mitochondrial Precursor" (Mouse) Amino acid residues 1–338 disclosed on Jul. 1, 1989.*
Fine et al. "Subcellular distribution and partial characterization of gingival mitochondrial and soluble malate dehydrogenases" J. Periodonatal Res. vol. 13, pp. 215–223, May 1978.*
J.M Wilkinson "Fragmentation of Polypeptides by Enzymic Methods" in Practical Protein Chemistry—A Handbook, Edited by A Darbre, Published by John Wiley & Sons, 1986.*
Tanaka, T. et al., "Molecular Cloning and Mapping of a Human cDNA for Cytosolic Malate Dehydrogenase (MDH1)", *Genomics*, 32: 128–130 (1996).
Loeber, G. et al., "Human NAD$^+$–dependent Mitochondrial Malic Enzyme—cDNA Cloning, Primary Structure, and Expression in *Escherichia Coli*", *J. Biol. Chem.*, 266: 3016–3021 (1991).
Chou, W.Y. et al., "Nonidentity of the cDNA Sequence of Human Breast Cancer Cell Malic Enzyme to that from the Normal Human Cell", *J. Protein Chem.*, 15: 273–279 (1996).

Loeber, G. et al., "Purification, cDNA cloning and heterologous expression of the human mitochondrial NADP$^+$–dependent malic enzyme", *Biochem. J.*, 304: 687–692 (1994).
Grant, P.M. et al., "Isolation and nucleotide sequence of a cDNA clone encoding rat mitochondrial malate dehydrogenase", *Nucleic Acids Res.*, 14: 6053–6066 (1986).
Joh, T. et al., "Cloning and Sequence Analysis of cDNAs Encoding Mammalian Mitochondrial Malate Dehydrogenase", *Biochemistry*, 26: 2515–2520 (1987) (GI 56643; GI 164541).
Joh, T. et al., "Cloning and Sequence Analysis of cDNAs Encoding Mammalian Cytosolic Malate Dehydrogenase—Comparison Of The Amino Acid Sequences Of Mammalian And Bacterial Malate Dehydrogenase", *J. Biol. Chem.*, 262: 15127–15131 (1987).
Scrutton, N.S. et al., "Redesign of the coenzyme specificity of a dehydrogenase by protein engineering", *Nature*, 343: 38–43 (1990).
Muchi, H. et al., "Studies on Mitochondrial and Cytoplasmic Malate Dehydrogenase in Childhood Myelodysplastic Syndrome", *Blood*, 62: 808–814 (1983).
Wiśniewska, W. et al., "Malate dehydrogenase and its isoenzymes in the peripheral blood leukocytes in progressive muscular dystrophy of the Duchenne type", *Neurol. Neurochir. Pol.*, 19: 318–322 (1985) (article in Polish, abstract in English).
Balinsky, D. et al., "Enzyme Activities in Normal, Dysplastic, and Cancerous Human Breast Tissues", *J. Natl. Cancer Inst.*, 72: 217–224 (1984).
Wagenknecht, K. et al., "Malate dehydrogenase isoenzymes in myocardial infarction", *Kardiologiia*, 28: 55–57 (1988) (rticle in Russian, abstract in English).
Kawai, M. et al., "Clinical Usefulness of Malate Dehydrogenase and its Mitochondrial Isoenzyme in Comparison with Aspartate Aminotransferase and its Mitochondrial Isoenzyme in Sera of Patients with Liver Disease", *Clin. Biochem.*, 23: 327–334 (1990).

* cited by examiner

Primary Examiner—Nashaat T. Nashed
Assistant Examiner—Christian L. Fronda
(74) Attorney, Agent, or Firm—Incyte Genomics, Inc.

(57) ABSTRACT

The invention provides a human mitochondrial malate dehydrogenase (MT-MDH) and polynucleotides which identify and encode MT-MDH. The invention also provides expression vectors, host cells, agonists, antibodies and antagonists. The invention also provides methods for treating disorders associated with expression of MT-MDH.

5 Claims, 10 Drawing Sheets

```
5'  G GCC CCA GAG AGC AGG CGC TGG GCA GTG TGG AGG TCG TTG GAG TCA CTT CCG
      9                 18              27              36              45              54

CGT CAC CAG CTC CTG TGC CTG CCA GTC GGT GCC CCT CCC GCT CCA GCC ATG CTC
     63              72              81              90              99             108
                                                                          M   L

TCC GCC CTC GCC CGG CCT GCC AGC GCT CTC GCG AGC CGC TTC AGC ACC TCG CAG
    117             126             135             144             153             162
     S   A   L   A   R   P   A   S   A   L   A   R   R   S   F   S   T   S

GCC CAG AAT GCT AAA GTA GCT GTG CTA GGG GCC TCT GGA ATC GGG CAG
    171             180             189             198             207             216
     A   Q   N   A   K   V   A   V   L   G   A   S   G   I   G   Q

CCA CTT TCA CTT CTC CTG AAG AAC AGC CCC TTG GTG AGC CGC ACC CTC TAT
    225             234             243             252             261             270
     P   L   S   L   L   K   N   S   P   L   V   S   R   T   L   Y

GAT ATC GCG CAC ACA CCC GGA GTG GCC GCA GAT CTG AGC CAC ATC GAG ACC AAA
    279             288             297             306             315             324
     D   I   A   H   T   P   G   V   A   A   D   L   S   H   I   E   T   K

GCC GCT GTG AAA GGC TAC CTC GGA CCT GAA CAG CTG CCT GAC TGC CTG AAA GGT
    333             342             351             360             369             378
     A   A   V   K   G   Y   L   G   P   E   Q   L   P   D   C   L   K   G
```

FIGURE 1A

```
                387         396         405         414         423         432
TGT GAT GTG GTA GTT ATT CCG GCT GGA GTC CCC AGA AAG CCA GGC ATG ACC CGG
 C   D   V   V   V   I   P   A   G   V   P   R   K   P   G   M   T   R 441         450         459         468         477         486
GAC GAC CTG TTC AAC ACC AAT GCC ACG ATT GTG GCC ACC CTG ACC GCT GCC TGT
 D   D   L   F   N   T   N   A   T   I   V   A   T   L   T   A   A   C 495         504         513         522         531         540
GCC CAG CAC TGC CCG GAA GCC ATG ATC TGC GTC ATT GCC AAT CCG GTT AAT TCC
 A   Q   H   C   P   E   A   M   I   C   V   I   A   N   P   V   N   S 549         558         567         576         585         594
ACC CCC ATC ACA GCA GAA GTT TTC AAG AAG CAT GGA GTG TAC AAC CCC AAC
 T   P   I   T   A   E   V   F   K   K   H   G   V   Y   N   P   N 603         612         621         630         639         648
AAA ATC TTC GGC GTG ACG ACC CTG GAC ATC GTC AGA GCC AAC ACC TTT GTT GCA
 K   I   F   G   V   T   T   L   D   I   V   R   A   N   T   F   V   A 657         666         675         684         693         702
GAG CTG AAG GGT TTG GAT CCA GCT CGA GTC AAC GTC CCT GTC ATT GGT GGC CAT
 E   L   K   G   L   D   P   A   R   V   N   V   P   V   I   G   G   H 711         720         729         738         747         756
GCT GGG AAG ACC ATC ATC CCC CTG ATC TCT CAG TGC ACC CCC AAG GTG GAC TTT
 A   G   K   T   I   I   P   L   I   S   Q   C   T   P   K   V   D   F
```

FIGURE 1B

```
      765            774            783            792            801            810
CCC CAG GAC CAG CTG ACA GCA CTC ACT GGG CGG ATC CAG GAG GCC GGC ACG GAG
 P   Q   D   Q   L   T   A   L   T   G   R   I   Q   E   A   G   T   E 819            828            837            846            855            864
GTG GTC AAG GCT AAA GCC GGA GCA GGC TCT GCC ACC CTC TCC ATG GCG TAT GCC
 V   V   K   A   K   A   G   A   G   S   A   T   L   S   M   A   Y   A 873            882            891            900            909            918
GGC GCC CGC TTT GTC TCC CTT GTG GAT GCA ATG AAT GGA AAG GAA GGT GTT
 G   A   R   F   V   S   L   V   D   A   M   N   G   K   E   G   V 927            936            945            954            963            972
GTG GAA TGT TCC TTC GTT AAG TCA CAG GAA ACG GAA TGT ACC TAC TTC TCC ACA
 V   E   C   S   F   V   K   S   Q   E   T   E   C   T   Y   F   S   T 981            990            999            1008           1017           1026
CCG CTG CTG GGG CTT GGG AAA AAG GGC ATC GAG AAG AAC CTG GGC ATC CCC GAG AAA GTC
 P   L   L   G   L   G   K   K   G   I   E   K   N   L   G   I   P   E   K   V 1035           1044           1053           1062           1071           1080
TCC TCT TTT GAG GAG AAG ATG ATC TCG GAT GCC ATC CCC GAG CTG AAG GCC TCC
 S   S   F   E   E   K   M   I   S   D   A   I   P   E   L   K   A   S 1089           1098           1107           1116           1125           1134
ATC AAG GGG GAA GAT TTC GTG AAG ACC CTG AAG TGA GCC GCT GTG ACG GGT
 I   K   G   E   D   F   V   K   T   L   K
```

FIGURE 1C

```
          1143           1152           1161           1170           1179           1188
GGC CAG TTT CCT TAA TTT ATG AAG GCA TCA TGT CAC TGC AAA GCC GTT GCA GAT 1197           1206           1215           1224           1233           1242
AAA CTT TGT ATT TTA ATT TGC TTT GGT GAT GAT TAC TGT ATT GAC ATC ATC ATG 1251           1260           1269           1278           1287           1296
CCT TCC AAA TTG TGG GTG GCT CTG TGG GCG CAT CAA TAA AAG CCG TCC TTG ATT 1305           1314           1323           1332
TTA TTT TTC AAG GTC CCT TCT GTA AAT GCA AAA AAA AAA A 3'
```

FIGURE 1D

| | | |
|---|---|---|
| 1 | M L S A L A R P A S A A L R R S F S T S | 11587 |
| 1 | M L S A L A R P V G A A L R R S F S T S | GI 56643 |
| 1 | - - - - - - - - - - - - - - - - - - - - | GI 164541 |
| 21 | A Q N N A K V A V L G A S G G I G Q P L | 11587 |
| 21 | A Q N N A K V A V L G A S G G I G Q P L | GI 56643 |
| 1 | - - - - - - - - - - - - - - - - - - - - | GI 164541 |
| 41 | S L L L K N S P L V S R L T L Y D I A H | 11587 |
| 41 | S L L L K N S P L V S R L T L Y D I A H | GI 56643 |
| 1 | S L L L K N S P L V S R L T L Y D I A H | GI 164541 |
| 61 | T P G V A A D L S H I E T K A A V K G Y | 11587 |
| 61 | T P G V A A D L S H I E T R A N V K G Y | GI 56643 |
| 21 | T P G V A A D L S H I E T R A T V K G Y | GI 164541 |
| 81 | L G P E Q L P D C L K G C D V V V I P A | 11587 |
| 81 | L G P E Q L P D C L K G C D V V V I P A | GI 56643 |
| 41 | L G P E Q L P D C L K G C D V V V I P A | GI 164541 |
| 101 | G V P R K P G M T R D D L F N T N A T I | 11587 |
| 101 | G V P R K P G M T R D D L F N T N A T I | GI 56643 |
| 61 | G V P R K P G M T R D D L F N T N A T M | GI 164541 |
| 121 | V A T L T A A C A Q H C P E A M I C V I | 11587 |
| 121 | V A T L T A A C A Q H C P E A M I C I I | GI 56643 |
| 81 | V A T L T V A C A Q H C P D A M I C I I | GI 164541 |
| 141 | A N P V N S T I P I T A E V F K K H G V | 11587 |
| 141 | S N P V N S T I P I T A E V F K K H G V | GI 56643 |
| 101 | S N P V N S T I P M T A E V F K K H G V | GI 164541 |
| 161 | Y N P N K I F G V T T L D I V R A N T F | 11587 |
| 161 | Y N P N K I F G V T T L D I V R A N T F | GI 56643 |
| 121 | Y N P N K I F G V T T L D I V R A N A F | GI 164541 |

FIGURE 2A

| | | |
|---|---|---|
| 181 | V A E L K G L D P A R V N V P V I G G H | 11587 |
| 181 | V A E L K G L D P A R V N V P V I G G H | GI 56643 |
| 141 | V A E L K G L D P A R V S V P V I G G H | GI 164541 |

| | | |
|---|---|---|
| 201 | A G K T I I P L I S Q C T P K V D F P Q | 11587 |
| 201 | A G K T I I P L I S Q C T P K V D F P Q | GI 56643 |
| 161 | A G K T I I P L I S Q C T P K V D F P Q | GI 164541 |

| | | |
|---|---|---|
| 221 | D Q L T A L T G R I Q E A G T E V V K A | 11587 |
| 221 | D Q L A T L T G K I Q E A G T E V V K A | GI 56643 |
| 181 | D Q L S T L T G R I Q E A G T E V V K A | GI 164541 |

| | | |
|---|---|---|
| 241 | K A G A G S A T L S M A Y A G A R F V F | 11587 |
| 241 | K A G A G S A T L S M A Y A G A R F V F | GI 56643 |
| 201 | K A G A G S A T L S M A Y A G A R F V F | GI 164541 |

| | | |
|---|---|---|
| 261 | S L V D A M N G K E G V V E C S F V K S | 11587 |
| 261 | S L V D A M N G K E G V I E C S F V Q S | GI 56643 |
| 221 | S L V D A M N G K E G V V E C S F V K S | GI 164541 |

| | | |
|---|---|---|
| 281 | Q E T E C T Y F S T P L L L G K K G I E | 11587 |
| 281 | K E T E C T Y F S T P L L L G K K G L E | GI 56643 |
| 241 | Q E T D C P Y F S T P L L L G K K G I E | GI 164541 |

| | | |
|---|---|---|
| 301 | K N L G I G K V S S F E E K M I S D A I | 11587 |
| 301 | K N L G I G K I T P F E E K M I A E A I | GI 56643 |
| 261 | K N L R I G K I S P F E E K M I A E A I | GI 164541 |

| | | |
|---|---|---|
| 321 | P E L K A S I K K G E D F V K T L K | 11587 |
| 321 | P E L K A S I K K G E D F V K N M K | GI 56643 |
| 281 | P E L K A S I K K G E E F V K N T K | GI 164541 |

241 K A G A G S A T L S M A Y A G A R F V F    11587
    - - G X G X X G X X X X X X X X X G       NAD(H)  mot.
    - - G X G X X A X X X A X X X X X G       NADP(H) mot.

```
                            SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 338 amino acids
          (B) TYPE: amino acid
          (C) STRANDEDNESS: single
          (D) TOPOLOGY: linear (vii) IMMEDIATE SOURCE:
          (A) LIBRARY: THP1PLB01
          (B) CLONE: 11587

(xi) SEQUENCE DESCRIPTION: SEQ ID NO:1:

Met Leu Ser Ala Leu Ala Arg Pro Ala Ser Ala Ala Leu Arg Arg Ser
 1               5                  10                  15

Phe Ser Thr Ser Ala Gln Asn Asn Ala Lys Val Ala Val Leu Gly Ala
                20                  25                  30

Ser Gly Gly Ile Gly Gln Pro Leu Ser Leu Leu Lys Asn Ser Pro
            35                  40                  45

Leu Val Ser Arg Leu Thr Leu Tyr Asp Ile Ala His Thr Pro Gly Val
 50                  55                  60

Ala Ala Asp Leu Ser His Ile Glu Thr Lys Ala Ala Val Lys Gly Tyr
65                  70                  75                  80

Leu Gly Pro Glu Gln Leu Pro Asp Cys Leu Lys Gly Cys Asp Val Val
                85                  90                  95

Val Ile Pro Ala Gly Val Pro Arg Lys Pro Gly Met Thr Arg Asp Asp
               100                 105                 110

Leu Phe Asn Thr Asn Ala Thr Ile Val Ala Thr Leu Thr Ala Ala Cys
               115                 120                 125

Ala Gln His Cys Pro Glu Ala Met Ile Cys Val Ile Ala Asn Pro Val
    130                 135                 140

Asn Ser Thr Ile Pro Ile Thr Ala Glu Val Phe Lys Lys His Gly Val
145                 150                 155                 160

Tyr Asn Pro Asn Lys Ile Phe Gly Val Thr Thr Leu Asp Ile Val Arg
                165                 170                 175

Ala Asn Thr Phe Val Ala Glu Leu Lys Gly Leu Asp Pro Ala Arg Val
                180                 185                 190

Asn Val Pro Val Ile Gly Gly His Ala Gly Lys Thr Ile Ile Pro Leu
            195                 200                 205

Ile Ser Gln Cys Thr Pro Lys Val Asp Phe Pro Gln Asp Gln Leu Thr
    210                 215                 220

Ala Leu Thr Gly Arg Ile Gln Glu Ala Gly Thr Glu Val Val Lys Ala
225                 230                 235                 240

Lys Ala Gly Ala Gly Ser Ala Thr Leu Ser Met Ala Tyr Ala Gly Ala
                245                 250                 255

Arg Phe Val Phe Ser Leu Val Asp Ala Met Asn Gly Lys Glu Gly Val
                260                 265                 270
```

```
Val Glu Cys Ser Phe Val Lys Ser Gln Thr Glu Cys Thr Tyr Phe
        275                 280                 285

Ser Thr Pro Leu Leu Gly Lys Lys Gly Ile Glu Lys Asn Leu Gly
        290                 295                 300

Ile Gly Lys Val Ser Ser Phe Glu Lys Met Ile Ser Asp Ala Ile
305                 310                 315                 320

Pro Glu Leu Lys Ala Ser Ile Lys Lys Gly Glu Asp Phe Val Lys Thr
                325                 330                 335

Leu Lys
```

(2) INFORMATION FOR SEQ ID NO:2:

(i) SEQUENCE CHARACTERISTICS:
        (A) LENGTH: 1334 base pairs
        (B) TYPE: nucleic acid
        (C) STRANDEDNESS: single
        (D) TOPOLOGY: linear (vii) IMMEDIATE SOURCE:
        (A) LIBRARY: THP1PLB01
        (B) CLONE: 11587

(xi) SEQUENCE DESCRIPTION: SEQ ID NO:2:

```
GGCCCCAGAG AGCAGGCGCT GGGCAGTGTG GAGGTCGTTG GAGTCACTTC CGCGTCACCA      60
GCTCCTGTGC CTGCCAGTCG GTGCCCCTCC CGCTCCAGCC ATGCTCTCCG CCCTCGCCCG     120
GCCTGCCAGC GCTGCTCTCC GCCGCAGCTT CAGCACCTCG GCCCAGAACA ATGCTAAAGT     180
AGCTGTGCTA GGGGCCTCTG GAGGCATCGG GCAGCCACTT TCACTTCTCC TGAAGAACAG     240
CCCCTTGGTG AGCCGCCTGA CCCTCTATGA TATCGCGCAC ACACCCGGAG TGGCCGCAGA     300
TCTGAGCCAC ATCGAGACCA AAGCCGCTGT GAAAGGCTAC CTCGGACCTG AACAGCTGCC     360
TGACTGCCTG AAAGGTTGTG ATGTGGTAGT TATTCCGGCT GGAGTCCCCA GAAAGCCAGG     420
CATGACCCGG GACGACCTGT TCAACACCAA TGCCACGATT GTGGCCACCC TGACCGCTGC     480
CTGTGCCCAG CACTGCCCGG AAGCCATGAT CTGCGTCATT GCCAATCCGG TTAATTCCAC     540
CATCCCCATC ACAGCAGAAG TTTTCAAGAA GCATGGAGTG TACAACCCCA ACAAAATCTT     600
CGGCGTGACG ACCCTGGACA TCGTCAGAGC CAACACCTTT GTTGCAGAGC TGAAGGGTTT     660
GGATCCAGCT CGAGTCAACG TCCCTGTCAT TGGTGGCCAT GCTGGGAAGA CCATCATCCC     720
CCTGATCTCT CAGTGCACCC CCAAGGTGGA CTTTCCCCAG GACCAGCTGA CAGCACTCAC     780
TGGGCGGATC CAGGAGGCCG GCACGGAGGT GGTCAAGGCT AAAGCCGGAG CAGGCTCTGC     840
CACCCTCTCC ATGGCGTATG CCGGCGCCCG CTTTGTCTTC TCCCTTGTGG ATGCAATGAA     900
TGGAAAGGAA GGTGTTGTGG AATGTTCCTT CGTTAAGTCA CAGGAAACGG AATGTACCTA     960
CTTCTCCACA CCGCTGCTGC TTGGGAAAAA GGGCATCGAG AAGAACCTGG GCATCGGCAA    1020
AGTCTCCTCT TTTGAGGAGA AGATGATCTC GGATGCCATC CCCGAGCTGA AGGCCTCCAT    1080
CAAGAAGGGG GAAGATTTCG TGAAGACCCT GAAGTGAGCC GCTGTGACGG GTGGCCAGTT    1140
TCCTTAATTT ATGAAGGCAT CATGTCACTG CAAAGCCGTT GCAGATAAAC TTTGTATTTT    1200
AATTTGCTTT GGTGATGATT ACTGTATTGA CATCATCATG CCTTCCAAAT TGTGGGTGGC    1260
TCTGTGGGCG CATCAATAAA AGCCGTCCTT GATTTTATTT TTCAAGGTCC CTTCTGTAAA    1320
TGCAAAAAAA AAAA                                                     1334
```

(2) INFORMATION FOR SEQ ID NO:3:

(i) SEQUENCE CHARACTERISTICS:

```
      (A) LENGTH: 338 amino acids
      (B) TYPE: amino acid
      (C) STRANDEDNESS: single
      (D) TOPOLOGY: linear (vii) IMMEDIATE SOURCE:
      (A) LIBRARY: GenBank
      (B) CLONE: 56643

(xi) SEQUENCE DESCRIPTION: SEQ ID NO:3:

Met Leu Ser Ala Leu Ala Arg Pro Val Gly Ala Ala Leu Arg Arg Ser
 1               5                  10                  15

Phe Ser Thr Ser Ala Gln Asn Asn Ala Lys Val Ala Val Leu Gly Ala
            20                  25                  30

Ser Gly Gly Ile Gly Gln Pro Leu Ser Leu Leu Leu Lys Asn Ser Pro
        35                  40                  45

Leu Val Ser Arg Leu Thr Leu Tyr Asp Ile Ala His Thr Pro Gly Val
    50                  55                  60

Ala Ala Asp Leu Ser His Ile Glu Thr Arg Ala Asn Val Lys Gly Tyr
65                  70                  75                  80

Leu Gly Pro Glu Gln Leu Pro Asp Cys Leu Lys Gly Cys Asp Val Val
                85                  90                  95

Val Ile Pro Ala Gly Val Pro Arg Lys Pro Gly Met Thr Arg Asp Asp
            100                 105                 110

Leu Phe Asn Thr Asn Ala Thr Ile Val Ala Thr Leu Thr Ala Ala Cys
        115                 120                 125

Ala Gln His Cys Pro Glu Ala Met Ile Cys Ile Ile Ser Asn Pro Val
    130                 135                 140

Asn Ser Thr Ile Pro Ile Thr Ala Glu Val Phe Lys Lys His Gly Val
145                 150                 155                 160

Tyr Asn Pro Asn Lys Ile Phe Gly Val Thr Thr Leu Asp Ile Val Arg
                165                 170                 175

Ala Asn Thr Phe Val Ala Glu Leu Lys Gly Leu Asp Pro Ala Arg Val
            180                 185                 190

Asn Val Pro Val Ile Gly Gly His Ala Gly Lys Thr Ile Ile Pro Leu
        195                 200                 205

Ile Ser Gln Cys Thr Pro Lys Val Asp Phe Pro Gln Asp Gln Leu Ala
    210                 215                 220

Thr Leu Thr Gly Lys Ile Gln Glu Ala Gly Thr Glu Val Val Lys Ala
225                 230                 235                 240

Lys Ala Gly Ala Gly Ser Ala Thr Leu Ser Met Ala Tyr Ala Gly Ala
                245                 250                 255

Arg Phe Val Phe Ser Leu Val Asp Ala Met Asn Gly Lys Glu Gly Val
            260                 265                 270

Ile Glu Cys Ser Phe Val Gln Ser Lys Glu Thr Glu Cys Thr Tyr Phe
        275                 280                 285

Ser Thr Pro Leu Leu Leu Gly Lys Lys Gly Leu Glu Lys Asn Leu Gly
    290                 295                 300

Ile Gly Lys Ile Thr Pro Phe Glu Glu Lys Met Ile Ala Glu Ala Ile
305                 310                 315                 320

Pro Glu Leu Lys Ala Ser Ile Lys Lys Gly Glu Asp Phe Val Lys Asn
                325                 330                 335

Met Lys
```

(2) INFORMATION FOR SEQ ID NO:4:

```
    (i) SEQUENCE CHARACTERISTICS:
        (A) LENGTH: 298 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 164541

(xi) SEQUENCE DESCRIPTION: SEQ ID NO:4:

Ser Leu Leu Leu Lys Asn Ser Pro Leu Val Ser Arg Leu Thr Leu Tyr
 1               5                  10                  15

Asp Ile Ala His Thr Pro Gly Val Ala Ala Asp Leu Ser His Ile Glu
                 20                  25                  30

Thr Arg Ala Thr Val Lys Gly Tyr Leu Gly Pro Glu Gln Leu Pro Asp
             35                  40                  45

Cys Leu Lys Gly Cys Asp Val Val Ile Pro Ala Gly Val Pro Arg
 50                  55                  60

Lys Pro Gly Met Thr Arg Asp Asp Leu Phe Asn Thr Asn Ala Thr Met
 65                  70                  75                  80

Val Ala Thr Leu Thr Val Ala Cys Ala Gln His Cys Pro Asp Ala Met
                 85                  90                  95

Ile Cys Ile Ile Ser Asn Pro Val Asn Ser Thr Ile Pro Met Thr Ala
                100                 105                 110

Glu Val Phe Lys Lys His Gly Val Tyr Asn Pro Asn Lys Ile Phe Gly
                115                 120                 125

Val Thr Thr Leu Asp Ile Val Arg Ala Asn Ala Phe Val Ala Glu Leu
                130                 135                 140

Lys Gly Leu Asp Pro Ala Arg Val Ser Val Pro Val Ile Gly Gly His
145                 150                 155                 160

Ala Gly Lys Thr Ile Ile Pro Leu Ile Ser Gln Cys Thr Pro Lys Val
                165                 170                 175

Asp Phe Pro Gln Asp Gln Leu Ser Thr Leu Thr Gly Arg Ile Gln Glu
                180                 185                 190

Ala Gly Thr Glu Val Val Lys Ala Lys Ala Gly Ala Gly Ser Ala Thr
                195                 200                 205

Leu Ser Met Ala Tyr Ala Gly Ala Arg Phe Val Phe Ser Leu Val Asp
210                 215                 220

Ala Met Asn Gly Lys Glu Gly Val Val Glu Cys Ser Phe Val Lys Ser
225                 230                 235                 240

Gln Glu Thr Asp Cys Pro Tyr Phe Ser Thr Pro Leu Leu Leu Gly Lys
                245                 250                 255

Lys Gly Ile Glu Lys Asn Leu Arg Ile Gly Lys Ile Ser Pro Phe Glu
                260                 265                 270

Glu Lys Met Ile Ala Glu Ala Ile Pro Glu Leu Lys Ala Ser Ile Lys
                275                 280                 285

Lys Gly Glu Glu Phe Val Lys Asn Thr Lys
290                 295
```

HUMAN MITOCHONDRIAL MALATE DEHYDROGENASE

FIELD OF THE INVENTION

This invention relates to nucleic acid and amino acid sequences of a human mitochondrial malate dehydrogenase and to the use of these sequences in the diagnosis, prevention, and treatment of developmental, vesicle trafficking, immunological, and neoplastic disorders.

BACKGROUND OF THE INVENTION

Nicotinamide adenine dinucleotides are involved in a very large number of oxidoreduction reactions both in the cytosol and in mitochondria. In general, they are not tightly bound to enzymes and are best considered as substrates, although they are often referred to as coenzymes. Nicotinamide adenine dinucleotide ($NAD^+$) and nicotinamide adenine dinucleotide phosphate ($NADP^+$) undergo reversible reduction to NADH and NADPH, respectively, but fulfill different roles in the cell. The major role of NADH is to transfer electrons from metabolic intermediates in a large number of biosynthetic processes into the electron transfer chain. NADPH acts as a reducing agent in a large number of biosynthetic processes.

The conversion of one molecule of glucose to two pyruvate in glycolysis generates two molecules of NADH. Since the amount of $NAD^+$ in the cell is limited, it is essential for the continuation of glycolysis that $NAD^+$ is rapidly reformed from the NADH produced. The inner mitochondrial membrane is impermeable to oxaloacetate, NADH and $NAD^+$, and there is no mitochondrial transport system for these molecules. This means that mitochondrial oxaloacetate is not replenished from the cytosol, nor does the NADH formed in the cytosol by glycolysis have access to the electron transfer chain. Depletion of mitochondrial $NAD^+$ alters the low $NA^+$/NADH ratio essential for the reduction of the electron transfer chain flavin carriers. The biochemical impasse is resolved by the cell through the use of 'substrate shuttles' which transport hydrogen atoms across the mitochondrial membranes. These shuttles comprise a reaction between NADH and an oxidized substrate in the cytosol, followed by transport of the reduced substrate into the mitochondrion. The reduced substrate is then oxidized by the electron transfer chain.

Elimination of toxic hydrogen peroxide which is synthesized as a metabolic byproduct within mitochondria is modulated by the reductant glutathione. Oxidized glutathione produced in some of these processes is reduced by NADPH through the action of glutathione reductase. Since NADPH cannot be transported through the inner mitochondrial membrane, it must be regenerated from endogenous $NADP^+$ to maintain low $NADP^+$/NADPH ratios. In erythrocytes, which have no mitochondria, NADPH is regenerated by glucose-6-phosphate dehydrogenase and phosphogluconate dehydrogenase. Glutamate dehydrogenase may be responsible for the regeneration of NADPH in the mitochondria, but this has not yet been proven. Cytosolic malate dehydrogenase converts malate and $NADP^+$ to pyruvate and NADPH as part of the pyruvate-malate shuttle. This shuttle is part of a pathway which enables mitochondrial acetyl coenzyme A to be transported via citrate to the cytosol to sites of fatty acid synthesis. A mitochondrial metabolic pathway in which malate is converted to pyruvate, with the concomitant conversion of $NADP^+$ to NADPH serves to regenerate NADPH and to increase levels of mitochondrial pyruvate in the absence of pyruvate import from the cytosolic sources.

Malate dehydrogenase, an $NAD(P)^+$-dependant dehydrogenase, in cooperation with aspartate aminotransferase isozymes, plays a pivotal role in the malate-aspartate shuttle and the pyruvate-malate shuttle. Regeneration of either mitochondrial NADH or NADPH is effected through the conversion of endogenous malate to pyruvate catalyzed by malate dehydrogenase. Four isoforms of the enzyme have been isolated from human tissue. Two human $NAD^+$-dependant malate dehydrogenase isoforms have been identified; one form is present in smooth muscle and striated muscle cytoplasm, the other in the mitochondria from rapidly proliferating and tumor cells (Tanaka, T. et al. (1996) Genomics 32:128–130; Loeber, G. et al. (1991) J. Biol. Chem. 266:3016–3021). Two $NADP^+$-dependant isoforms have also been identified in human breast cancer cell cytoplasm and in human hippocampal mitochondria (Chou, W. Y. (1996) J. Protein Chem. 15:272–279; Loeber, G. et al. (1994) Biochem. J. 304:687–692).

Most mitochondrial proteins, including malate dehydrogenase, are encoded by nuclear DNA. The enzyme is synthesized as a larger precursor molecule and subsequently transported into the mitochondria. An N-terminal region mediates recognition of protein targeted for this organanelle and is termed the "transit peptide". Upon binding and import to the mitochondrion, the transit peptide is removed by proteolysis and the subunits assemble to form active complexes (Grant, P. M. et al. (1986) Nucleic Acids Res. 14:6053–6066).

Two genes encoding murine malate dehydrogenase isoforms have been identified; one is a cytosolic isoform from heart and liver and the other is a mitochondrial isoform from liver. The protein products share 23% homology. Levels of mRNA encoding the mitochondrial isoform are elevated in heart, brain, and kidney, and are relatively low in liver (Joh, T. et al. (1987) Biochemistry 26:2515–2520; Joh, T. et al. (1987) J. Biol. Chem. 262:15127–15131).

The binding sites for $NAD^+$ and $NADP^+$ are similar in dehydrogenase enzymes isolated from organisms as diverse as bacteria, yeast, insects, and mammals, but those for $NADP^+$ differ from those that bind $NAD^+$ at certain amino acid residue positions. These differences are to accommodate the different charge distributions within the nicotinamide adenine dinucleotide substrates (Scrutton, N. S. et al. (1990) Nature 343:38–43).

Reduced mitochondrial malate dehydrogenase activity in polymorphonuclear cells has been associated with 7-monosomy myelodysplastic syndrome, and in peripheral blood leukocytes (PBL) from Duchenne muscular dystrophy (Muchi, H. and Yamamoto, Y (1983) Blood 62:808–814; Wisniewska, W. and Lukasiuk, M. (1985) Neurol. Neurochir. Pol. 19:318–322). Significantly increased levels of mitochondrial malate dehydrogenase have been found in human breast cancer tissue, in PBL following myocardial infarction, and in PBL associated with hepatocarcinoma and acute circulatory failure (Balinsky, D. et al. (1984) J. Natl. Cancer Inst. 72:217–224; Wagenknecht, K. et al. (1988) Kardiologiia 28:55–57; Kawai, M. and Hosaki, S. (1990) Clin. Biochem. 23:327–334).

The discovery of a new human mitochondrial malate dehydrogenase and the polynucleotides encoding it satisfies a need in the art by providing new compositions which are useful in the diagnosis, prevention and treatment of developmental, vesicle trafficking, immunological, and neoplastic disorders.

SUMMARY OF THE INVENTION

The invention features a substantially purified polypeptide, human mitochondrial malate dehydrogenase (MT-MDH), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding MT-MDH under conditions suitable for the expression of the polypeptide; and b) recovering the polypeptide from the host cell culture.

The invention also provides a pharmaceutical composition comprising a substantially purified MT-MDH having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a developmental disorder comprising administering to a subject in need of such treatment an effective amount of a pharmaceutical composition comprising purified MT-MDH.

The invention also provides a method for treating or preventing a vesicle trafficking disorder comprising administering to a subject in need of such treatment an effective amount of a pharmaceutical composition comprising purified MT-MDH.

The invention also provides a method for treating or preventing an immunological disorder comprising administering to a subject in need of such treatment an effective amount of an antagonist to MT-MDH.

The invention also provides a method for treating or preventing a neoplastic disorder comprising administering to a subject in need of such treatment an effective amount of an antagonist to MT-MDH.

The invention also provides a method for detecting a polynucleotide which encodes MT-MDH in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding MT-MDH in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of MT-MDH. The alignment was produced using MacDNASIS PRO™ software (Hitachi Software Engineering Co. Ltd. San Bruno, Calif.).

FIGS. 2A and 2B show the amino acid sequence alignments among MT-MDH (11587; SEQ ID NO:1), murine mitochondrial malate dehydrogenase (GI 56643; SEQ ID NO:3) and porcine mitochondrial malate dehydrogenase (GI 164541; SEQ ID NO:4), produced using the multisequence alignment program of DNASTAR™ software (DNASTAR Inc, Madison Wis.).

FIGS. 4A and 4B show the amino acid sequence alignments among MT-MDH (SEQ ID NO:1), the NAD(H) binding motif (NAD(H) mot.), and the NADP(H) binding motif (NADP(H) mot.), produced using the multisequence alignment program of DNASTAR™ software (DNASTAR Inc, Madison Wis.).

DESCRIPTION OF THE INVENTION

Figure 3A:
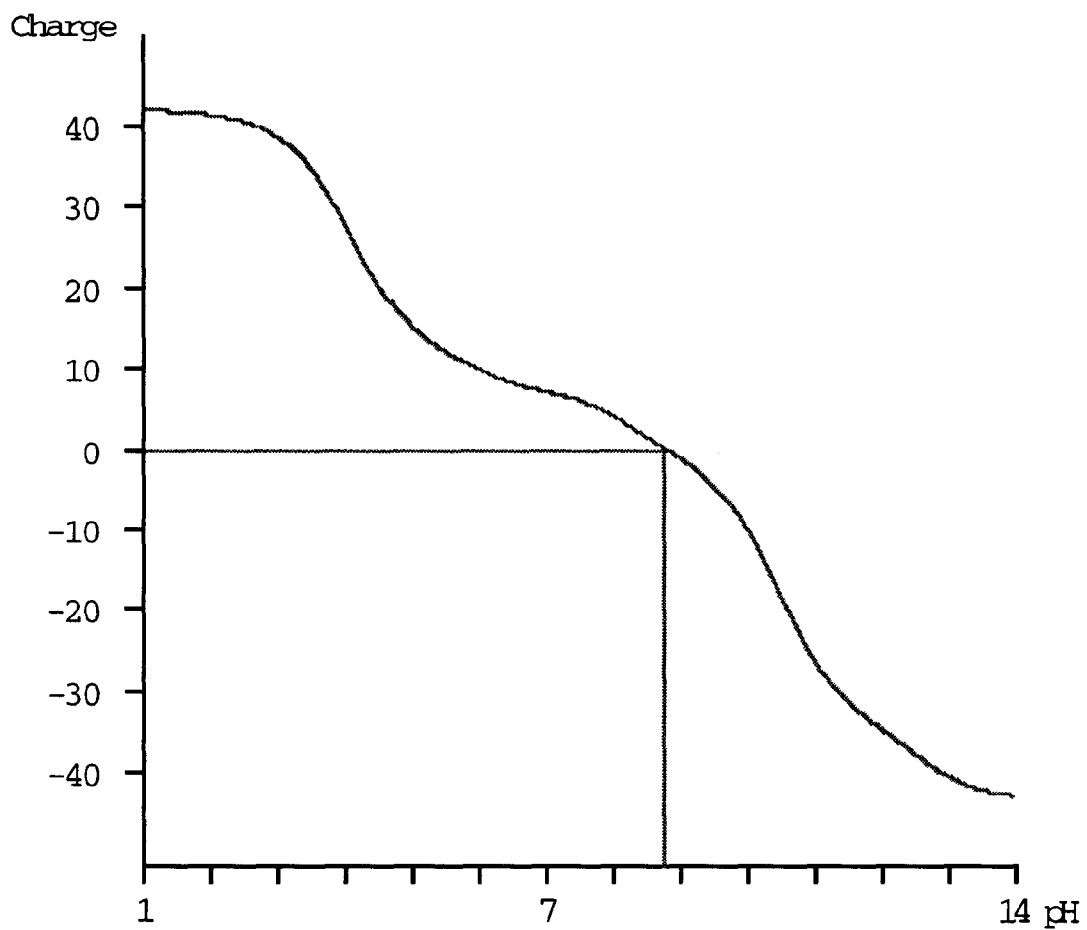
FIGS. 3A and 3B show the electrostatic plots for MT-MDH (SEQ ID NO:1) and murine malate dehydrogenase (SEQ ID NO:3), respectively; the positive X axis reflects pH, and the negative Y axis, residue side chain charge (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

MT-MDH, as used herein, refers to the amino acid sequences of substantially purified MT-MDH obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to MT-MDH, increases or prolongs the duration of the effect of MT-MDH. Agonists may include proteins, nucleic acids, carbohydrates, or any other molecules which bind to and modulate the effect of MT-MDH.

An "allele" or "allelic sequence", as used herein, is an alternative form of the gene encoding MT-MDH. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding MT-MDH as used herein include those with deletions, insertions, or substitutions of different nucleotides resulting in a polynucleotide that encodes the same or a functionally equivalent MT-MDH. Included within this definition are polymorphisms which may or may not be readily detectable using a particular oligonucleotide probe of the polynucleotide encoding MT-MDH, and improper or unexpected hybridization to alleles, with a locus other than the normal chromosomal locus for the polynucleotide sequence encoding MT-MDH. The encoded protein may also be "altered" and contain deletions, insertions, or substitutions of amino acid residues which produce a silent change and result in a functionally equivalent MT-MDH. Deliberate amino acid substitutions may be made on the basis of similarity in polarity, charge, solubility, hydrophobicity, hydrophilicity, and/or the amphipathic nature of the residues as long as the biological or immunological activity of MT-MDH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine. "Amino acid sequence" as used herein refers to an oligopeptide, peptide, polypeptide, or protein sequence, and fragment thereof, and to naturally occurring or synthetic molecules. Fragments of MT-MDH are preferably about 5 to 15 about amino acids in length and retain the biological activity or the immunological activity of MT-MDH. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to MT-MDH, decreases the amount or the duration of the effect of the biological or immunological activity of MT-MDH. Antagonists may include proteins, nucleic acids, carbohydrates, antibodies or any other molecules which decrease the effect of MT-MDH.

As used herein, the term "antibody" refers to intact molecules as well as fragments thereof, such as Fa, $F(ab')_2$, and Fv, which are capable of binding the epitopic determinant. Antibodies that bind MT-MDH polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic MT-MDH, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding MT-MDH (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding MT-MDH in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to MT-MDH or the encoded MT-MDH. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule. "Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of MT-MDH. For example, modulation may cause an increase or a decrease in protein activity, binding characteristics, or any other biological, functional or immunological properties of MT-MDH.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand.

"Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about to nucleotides, which can be used in PCR amplification or a hybridization assay, or a microarray. As used herein, oligonucleotide is substantially equivalent to the terms "amplimers", "primers", "oligomers", and "probes", as commonly defined in the art. "Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length MT-MDH and fragments thereof.

The term "sample", as used herein, is used in its broadest sense. A biological sample suspected of containing nucleic acid encoding MT-MDH, or fragments thereof, or MT-MDH itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of MT-MDH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human mitochondrial malate dehydrogenase (hereinafter referred to as "MT-MDH"), the polynucleotides encoding MT-MDH, and the use of these compositions for the diagnosis, prevention, or treatment of developmental, vesicle trafficking, immunological, and neoplastic disorders.

Nucleic acids encoding the MT-MDH of the present invention were first identified in Incyte Clone 11587 from the human peripheral promonocyte cell line cDNA library (THP1PLB01) using a computer search for amino acid sequence alignments. A consensus sequence, SEQ ID NO:2, was derived from the following overlapping and/or extended nucleic acid sequences: Incyte Clones 11587 (THP1PLB01), 263843 (HNT2AGT01), 307780 (HEARNOT01), 306240 (HEARNOT01), 893291 (STOMTUT01), and 289440 (TMLR3DT01).

Figure 3B:
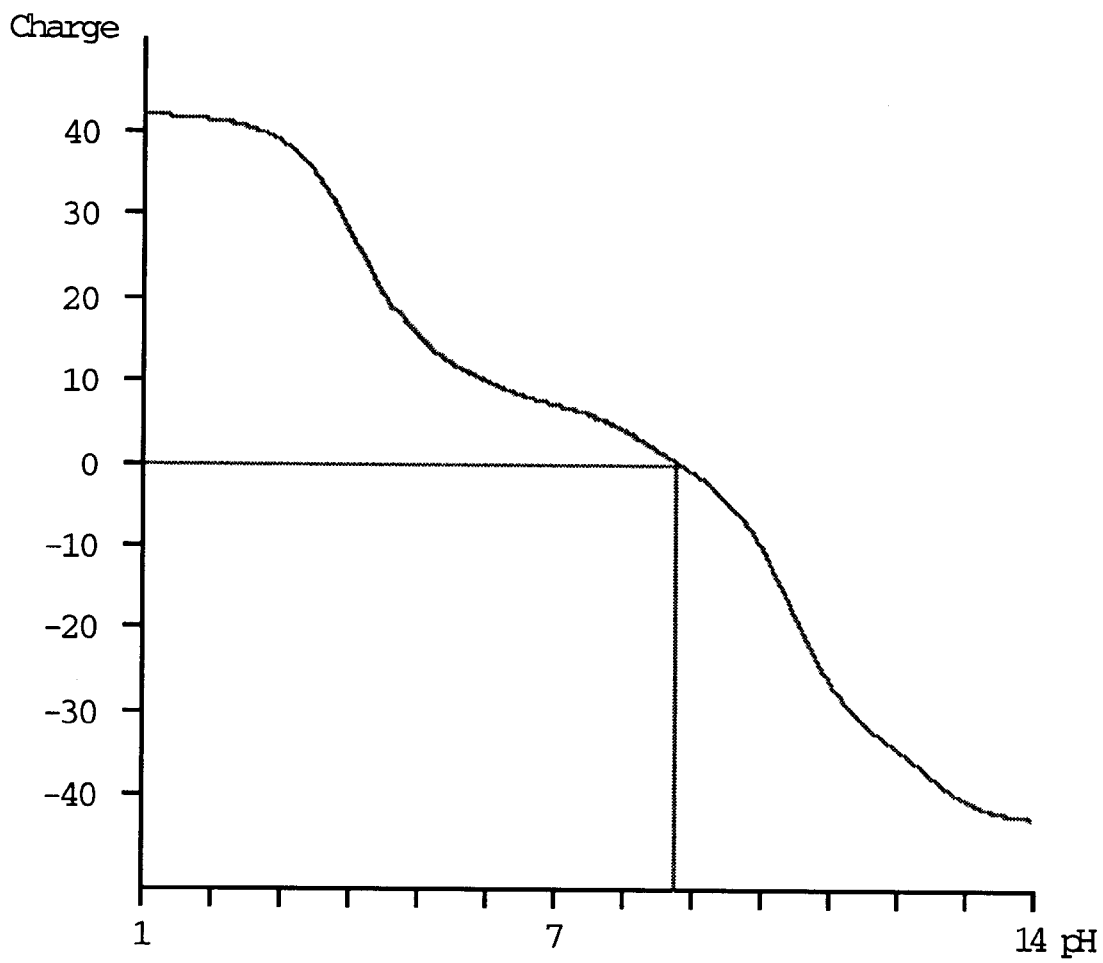

In one embodiment, the invention encompasses a polypeptide comprising the amino acid sequence of SEQ ID NO:1, as shown in FIGS. 1A, 1B, 1C, and 1D. MT-MDH is 294 amino acids in length and has two potential N-glycosylation sites at residues N-117 and N-145, seven potential casein kinase II phosphorylation sites at T-54, S-69, T-109, T-170, S-261, S-309, and S-310, four potential protein kinase C phosphorylation sites at residues T-213, T-227, S-326, and T-336, a malate dehydrogenase active site signature between residues V- 169 and V-181, and a transit peptide sequence from residues M-1 to N-24. As shown in FIGS. 2A and 2B, MT-MDH has chemical and structural homology with murine mitochondrial malate dehydrogenase (GI 56643; SEQ ID NO:3) and porcine mitochondrial malate dehydrogenase (GI 164541; SEQ ID NO:4). In particular, MT-MDH and murine mitochondrial malate dehydrogenase share 94% identity, share both potential N-glycosylation sites, six potential casein kinase II sites, three potential protein kinase C sites, the malate dehydrogenase active site signature, and the transit peptide sequence. As illustrated by FIGS. 3A and 3B, respectively, MT-MDH and murine mitochondrial malate dehydrogenase (SEQ ID NO:3) have similar isoelectric points (pI=8.8). As illustrated by FIGS. 4A and 4B, MT-MDH contains potential NAD(H) and NADP(H) binding site motifs. Northern analysis shows the expression of this sequence in various libraries, at least 49% of which are immortalized or cancerous and at least 24% of which involve immune response. Of particular note is the expression of MT-MDH in fetal tissues; in cardiovascular, gut, nervous, and reproductive tissues; and in secretory and hematopoietic tissues.

The invention also encompasses MT-MDH variants. A preferred MT-MDH variant is one having at least 80%, and more preferably at least 90%, amino acid sequence identity to the MT-MDH amino acid sequence (SEQ ID NO:1) and which retains at least one biological, immunological or other functional characteristic or activity of MT-MDH. A most preferred MT-MDH variant is one having at least 95% amino acid sequence identity to SEQ ID NO:1.

The invention also encompasses polynucleotides which encode MT-MDH. Accordingly, any nucleic acid sequence which encodes the amino acid sequence of MT-MDH can be used to produce recombinant molecules which express MT-MDH. In a particular embodiment, the invention encompasses the polynucleotide comprising the nucleic acid sequence of SEQ ID NO:2 as shown in FIGS. 1A, 1B, 1C, and 1D.

It will be appreciated by those skilled in the art that as a result of the degeneracy of the genetic code, a multitude of nucleotide sequences encoding MT-MDH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MT-MDH, and all such variations are to be considered as being specifically disclosed.

Although nucleotide sequences which encode MT-MDH and its variants are preferably capable of hybridizing to the nucleotide sequence of the naturally occurring MT-MDH under appropriately selected conditions of stringency, it may be advantageous to produce nucleotide sequences encoding MT-MDH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MT-MDH and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode MT-MDH and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding MT-MDH or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding MT-MDH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MT-MDH may be used in recombinant DNA molecules to direct expression of MT-MDH, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express MT-MDH.

As will be understood by those of skill in the art, it may be advantageous to produce MT-MDH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter MT-MDH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding MT-MDH may be ligated to a heterologous sequence to encode a fusion protein. For example, to screen peptide libraries for inhibitors of MT-MDH activity, it may be useful to encode a chimeric MT-MDH protein that can be recognized by a commercially available antibody. A fusion protein may also be engineered to contain a cleavage site located between the MT-MDH encoding sequence and the heterologous protein sequence, so that MT-MDH may be cleaved and purified away from the heterologous moiety.

In another embodiment, sequences encoding MT-MDH may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of MT-MDH, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of MT-MDH, or any part thereof, may be altered during direct synthesis and/or combined using chemical methods with sequences from other proteins, or any part thereof, to produce a variant polypeptide.

In order to express a biologically active MT-MDH, the nucleotide sequences encoding MT-MDH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MT-MDH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N. Y., and Ausubel, F. M. et al. (1989) *Current Protocols in Molecular Biology*, John Wiley & Sons, New York, N.Y.

A variety of expression vector/host systems may be utilized to contain and express sequences encoding MT-MDH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MT-MDH, vectors based on SV40 or EBV may be used with an appropriate selectable marker.

In bacterial systems, a number of expression vectors may be selected depending upon the use intended for MT-MDH. For example, when large quantities of MT-MDH are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding MT-MDH may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding MT-MDH may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express MT-MDH. For example, in one such system, *Autographa californica* nuclear polyhedrosis virus (AcNPV) is used as a vector to express foreign genes in *Spodoptera frugiperda* cells or in Trichoplusia larvae. The sequences encoding MT-MDH may be cloned into a non-essential region of the virus, such as the polyhedrin gene, and placed under control of the polyhedrin promoter. Successful insertion of MT-MDH will render-the polyhedrin gene inactive and produce recombinant virus lacking coat protein. The recombinant viruses may then be used to infect, for example, *S. frugiperda* cells or Trichoplusia larvae in which MT-MDH may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding MT-MDH may be ligated into an adenovirus transcription/translation complex consisting of the late promoter and tripartite leader sequence. Insertion in a non-essential E1 or E3 region of the viral genome may be used to obtain a viable virus which is capable of expressing MT-MDH in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding MT-MDH. Such signals include the ATG initiation codon and adjacent sequences. In cases where sequences encoding MT-MDH, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express MT-MDH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding MT-MDH is inserted within a marker gene sequence, transformed cells containing sequences encoding MT-MDH can be identified by the absence of marker gene function. Alternatively, a marker gene can be placed in tandem with a sequence encoding MT-MDH under the control of a single promoter. Expression of the marker gene in response to induction or selection usually indicates expression of the tandem gene as well.

Alternatively, host cells which contain the nucleic acid sequence encoding MT-MDH and express MT-MDH may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding MT-MDH can be detected by DNA-DNA or DNA-RNA hybridization or amplification using probes or fragments or fragments of polynucleotides encoding MT-MDH. Nucleic acid amplification based assays involve the use of oligonucleotides or oligomers based on the sequences encoding MT-MDH to detect transformants containing DNA or RNA encoding MT-MDH.

A variety of protocols for detecting and measuring the expression of MT-MDH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on MT-MDH is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MT-MDH include oligolabeling, nick translation, end-labeling or PCR amplification using a labeled nucleotide. Alternatively, the sequences encoding MT-MDH, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding MT-MDH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode MT-MDH may be designed to contain signal sequences which direct secretion of MT-MDH through a prokaryotic or eukaryotic cell membrane. Other constructions may be used to join sequences encoding MT-MDH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MT-MDH may be used to facilitate purification. One such expression vector provides for expression of a fusion protein containing MT-MDH and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying MT-MDH from the fusion protein. A discussion of vectors which contain fusion proteins is provided in Kroll, D. J. et al. (1993; DNA Cell Biol. 12:441–453).

In addition to recombinant production, fragments of MT-MDH may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of MT-MDH may be chemically synthesized separately and combined using chemical methods to produce the full length molecule.

Therapeutics

Chemical and structural homology exists among MT-MDH and murine and porcine mitochondrial malate dehydrogenases (GI 56643) and (GI 164541), respectively. In addition, MT-MDH is expressed in tumor, proliferating, and fetal tissues; in cardiovascular, gut, nervous, and reproductive tissues; and in secretory and hematopoietic tissues. Therefore, MT-MDH appears to play a role in developmental, vesicle trafficking, immunological, and neoplastic disorders. $NAD^+$- or $NADP^+$-dependant malate dehydrogenase isoforms have not yet been identified in the mitochondria of non-neuronal, quiescent human tissue.

Therefore, in one embodiment, MT-MDH or a fragment or derivative thereof may be administered to a subject to treat or prevent a developmental disorder. The term "developmental disorder" refers to any disorder associated with development or function of a tissue, organ, or system of a subject, i.e., brain, adrenal gland, kidney, skeletal or reproductive system. Such disorders include, but are not limited to, renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector capable of expressing MT-MDH, or a fragment or a derivative thereof, may also be administered to a subject to treat or prevent a developmental disorder including, but not limited to, those described above.

In still another embodiment, an agonist of MT-MDH may also be administered to a subject to treat or prevent a developmental disorder including, but not limited to, those described above.

In one embodiment, MT-MDH or a fragment or derivative thereof may be administered to a subject to treat or prevent a vesicle trafficking disorder. Such disorders include, but are not limited to, cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections.

In another embodiment, a vector capable of expressing MT-MDH, or a fragment or a derivative thereof, may also be administered to a subject to treat or prevent a vesicle trafficking disorder including, but not limited to, those listed above.

In still another embodiment, an agonist of MT-MDH may also be administered to a subject to treat or prevent a vesicle trafficking disorder including, but not limited to, those listed above.

In one embodiment, an antagonist of MT-MDH may be administered to a subject to prevent or treat or prevent an immunological disorder. Such immunological disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds MT-MDH may be used directly as an antagonist or indirectly as a targeting or delivery mechanism for bringing a pharmaceutical agent to cells or tissue which express MT-MDH.

In another embodiment, a vector expressing the complement of the polynucleotide encoding MT-MDH may be administered to a subject to treat or prevent an immunological disorder including, but not limited to, those described above.

In one embodiment, an antagonist of MT-MDH may be administered to a subject to prevent or treat or prevent a neoplastic disorder. Such disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds MT-MDH may be used directly as an antagonist or indirectly as a targeting or delivery mechanism for bringing a pharmaceutical agent to cells or tissue which express MT-MDH.

In another embodiment, a vector expressing the complement of the polynucleotide encoding MT-MDH may be administered to a subject to treat or prevent a neoplastic disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MT-MDH may be produced using methods which are generally known in the art. In particular, purified MT-MDH may be used to produce antibodies or to screen libraries of pharmaceutical agents to identify those which specifically bind MT-MDH.

Antibodies to MT-MDH may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with MT-MDH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MT-MDH have an amino acid sequence consisting of at least five amino acids and more preferably at least amino acids. It is also preferable that they are identical to a portion of the amino acid sequence of the natural protein, and they may contain the entire amino acid sequence of a small, naturally occurring molecule. Short stretches of MT-MDH amino acids may be fused with those of another protein such as keyhole limpet hemocyanin and antibody produced against the chimeric molecule.

Monoclonal antibodies to MT-MDH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce MT-MDH-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for MT-MDH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MT-MDH and its specific antibody. A two-site, monoclonal-based immunoassay utilizing monoclonal antibodies reactive to two non-interfering MT-MDH epitopes is preferred, but a competitive binding assay may also be employed (Maddox, supra).

In another embodiment of the invention, the polynucleotides encoding MT-MDH, or any fragment or complement thereof, may be used for therapeutic purposes. In one aspect, the complement of the polynucleotide encoding MT-MDH may be used in situations in which it would be desirable to block the transcription of the mRNA. In particular, cells may be transformed with sequences complementary to polynucleotides encoding MT-MDH. Thus, complementary molecules or fragments may be used to modulate MT-MDH activity, or to achieve regulation of gene function. Such technology is now well known in the art, and sense or antisense oligonucleotides or larger fragments, can be designed from various locations along the coding or control regions of sequences encoding MT-MDH.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding MT-MDH. These techniques are described both in Sambrook et al. (supra) and in Ausubel et al. (supra).

Genes encoding MT-MDH can be turned off by transforming a cell or tissue with expression vectors which express high levels of a polynucleotide or fragment thereof which encodes MT-MDH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding MT-MDH (signal sequence, promoters, enhancers, and introns). Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MT-MDH.

Specific ribozyme cleavage sites within any potential RNA target are initially identified by scanning the target molecule for ribozyme cleavage sites which include the following sequences: GUA, GUU, and GUC. Once identified, short RNA sequences of between and ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MT-MDH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MT-MDH, antibodies to MT-MDH, mimetics, agonists, antagonists, or inhibitors of MT-MDH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain i suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MT-MDH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MT-MDH or fragments thereof, antibodies of MT-MDH, agonists, antagonists or inhibitors of MT-MDH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting to pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MT-MDH may be used for the diagnosis of conditions or diseases characterized by expression of MT-MDH, or in assays to monitor patients being treated with MT-MDH, agonists, antagonists or inhibitors. The antibodies useful for diagnostic purposes may be prepared in the same manner as those described above for therapeutics. Diagnostic assays for MT-MDH include methods which utilize the antibody and a label to detect MT-MDH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MT-MDH are known in the art and provide a basis for diagnosing altered or abnormal levels of MT-MDH expression. Normal or standard values for MT-MDH expression are established by combining body fluids or cell extracts taken from normal mammalian subjects, preferably human, with antibody to MT-MDH under conditions suitable for complex formation The amount of standard complex formation may be quantified by various methods, but preferably by photometric, means. Quantities of MT-MDH expressed in subject, control and disease, samples from biopsied tissues are compared with the standard values. Deviation between standard and subject values establishes the parameters for diagnosing disease.

In another embodiment of the invention, the polynucleotides encoding MT-MDH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MT-MDH may be correlated with disease. The diagnostic assay may be used to distinguish between absence, presence, and excess expression of MT-MDH, and to monitor regulation of MT-MDH levels during therapeutic intervention.

In one aspect, hybridization with PCR probes which are capable of detecting polynucleotide sequences, including genomic sequences, encoding MT-MDH or closely related molecules, may be used to identify nucleic acid sequences which encode MT-MDH. The specificity of the probe, whether it is made from a highly specific region, e.g., unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MT-MDH, alleles, or related sequences.

Probes may also be used for the detection of related sequences, and should preferably contain at least 50% of the nucleotides from any of the MT-MDH encoding sequences. The hybridization probes of the subject invention may be DNA or RNA and derived from the nucleotide sequence of SEQ ID NO:2 or from genomic sequence including promoter, enhancer elements, and introns of the naturally occurring MT-MDH.

Means for producing specific hybridization probes for DNAs encoding MT-MDH include the cloning of nucleic acid sequences encoding MT-MDH or MT-MDH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding MT-MDH may be used for the diagnosis of conditions or disorders which are associated with expression of MT-MDH. Examples of such conditions or disorders include a developmental disorder such as renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss; a vesicle trafficking disorder such as cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections; an immunological disorder such as adult respiratory distress syndrome, anemia, atherosclerosis, bronchitis, cholecystitis, Crohn's disease, atopic dermatitis, dermatomyositis, emphysema, erythema nodosum, atrophic gastritis, glomerulonephritis, gout, hypereosinophilia, irritable bowel syndrome, myocardial or pericardial inflammation, osteoporosis, pancreatitis, polymyositis, Werner syndrome, and autoimmune thyroiditis; complications of cancer, hemodialysis, and extracorporeal circulation; or a neoplastic disorder such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding MT-MDH may be used in Southern or northern analysis, dot blot, or other membrane-based technologies; in PCR technologies; or in dipstick, pin, ELISA assays or microarrays utilizing fluids or tissues from patient biopsies to detect altered MT-MDH expression. Such qualitative or quantitative methods are well known in the art.

In a particular aspect, the nucleotide sequences encoding MT-MDH may be useful in assays that detect activation or induction of various cancers, particularly those mentioned above. The nucleotide sequences encoding MT-MDH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MT-MDH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MT-MDH, a normal or standard profile for expression is established. This may be accomplished by combining body fluids or cell extracts taken from normal subjects, either animal or human, with a sequence, or a fragment thereof, which encodes MT-MDH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MT-MDH may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MT-MDH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence.

The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode MT-MDH may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial PI constructions or single chromosome cDNA libraries as reviewed in Price, C. M. (1993) Blood Rev. 7:127–134, and Trask, B.J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding MT-MDH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, MT-MDH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between MT-MDH and the agent being tested, may be measured.

Another technique for drug screening which may be used provides for high throughput screening of compounds having suitable binding affinity to the protein of interest as described in published PCT application WO84/03564. In this method, as applied to MT-MDH large numbers of different small test compounds are synthesized on a solid substrate, such as plastic pins or some other surface. The test compounds are reacted with MT-MDH, or fragments thereof, and washed. Bound MT-MDH is then detected by methods well known in the art. Purified MT-MDH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MT-MDH specifically compete with a test compound for binding MT-MDH. In this manner, the antibodies can be used to detect the presence of any peptide which shares one or more antigenic determinants with MT-MDH.

In additional embodiments, the nucleotide sequences which encode MT-MDH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I THP1PLB01 cDNA Library Construction

The THP1PLB01 cDNA library was custom-constructed from activated human monocytes by Stratagene. Poly(A+) RNA was purified from THP-1 cells which were cultured for 48 hr with 100 nm TPA and activated with 1 μg/ml LPS after 4 hr. cDNA synthesis was primed separately with both oligo d(T) and random hexamers and the two cDNA libraries were treated separately. Synthetic adaptor oligonucleotides were ligated onto cDNA ends enabling insertion into Uni-ZAP™ vector system (Stratagene). Finally, the two libraries were combined into a single library by mixing equal numbers of bacteriophage.

The cDNA library can be screened with either DNA probes or antibody probes and the pBluescript® phagemid (Stratagene) can be rapidly excised in vivo. The custom-constructed library phage particles were transfected into *E. coli* host strain XL1-Blue® (Stratagene). Alternative unidirectional vectors include but are not limited to pcDNAI (Invitrogen, San Diego, Calif.) and pSHlox-1 (Novagen, Madison, Wis.).

II Isolation and Sequencing of cDNA Clones

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript® plasmid and the cDNA insert.

The phagemid DNA was secreted from the cells, purified, and used to re-infect fresh host cells, where the double stranded phagemid DNA was produced. Because the phagemid carries the gene for β-lactamase, the newly-transformed bacteria are selected on medium containing ampicillin.

Phagemid DNA was purified using the Magic Minipreps™ DNA Purification System (Promega catalogue #A7100; Promega, Madison, Wis.). The DNA was eluted from the purification resin already prepared for DNA sequencing and other analytical manipulations. Phagemid DNA was also purified using the QIAwell-8 Plasmid, QIAwell PLUS, and QIAwell ULTRA DNA Purification System (QIAGEN, Chatsworth, Calif.). The DNA was eluted from the purification resin already prepared for DNA sequencing and other analytical manipulations.

The cDNA inserts from random isolates were sequenced in part. Conventional enzymatic methods employ DNA polymerase Klenow fragment, Sequenase™ or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labeled precursors) or by fluorescence (for fluorescent-labelled precursors). Recent improvements in mechanized reaction preparation, sequencing and analysis using the fluorescent detection method have permitted expansion in the number of sequences that can be determined per day (such as the Applied Biosystems 373 DNA sequencer and Catalyst 800).

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J. Mol. Evol.* 36:290–300; Altschul, S. F. et al. (1990) *J. Mol. Evol.* 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MT-MDH occurs. Abundance and percent abundance are also reported. Abundance directly reflects the number of times a particular transcript is represented in a cDNA library, and percent abundance is abundance divided by the total number of sequences examined in the cDNA library.

V Extension of MT-MDH Encoding Polynucleotides

The nucleic acid sequence of the Incyte Clone 11587 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| Step 1  | 94° C. for 1 min (initial denaturation) |
|---------|------------------------------------------|
| Step 2  | 65° C. for 1 min                         |
| Step 3  | 68° C. for 6 min                         |
| Step 4  | 94° C. for 15 sec                        |
| Step 5  | 65° C. for 1 min                         |
| Step 6  | 68° C. for 7 min                         |
| Step 7  | Repeat step 4–6 for 15 additional cycles |
| Step 8  | 94° C. for 15 sec                        |
| Step 9  | 65° C. for 1 min                         |
| Step 10 | 68° C. for 7:15 min                      |
| Step 11 | Repeat step 8–10 for 12 cycles           |
| Step 12 | 72° C. for 8 min                         |
| Step 13 | 4° C. (and holding)                      |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate relaxation and cloning.

After ethanol precipitation, the products were redissolved in 13 µl of ligation buffer, 1 µl T4-DNA ligase (15units) and 1 µl T4 polynucleotide kinase were added, and the mixture was incubated at room temperature for 2–3 hours or overnight at 16° C. Competent E. coli cells (in 40 µl of appropriate media) were transformed with 3µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec                              |
|--------|------------------------------------------------|
| Step 2 | 94° C. for 20 sec                              |
| Step 3 | 55° C. for 30 sec                              |
| Step 4 | 72° C. for 90 sec                              |
| Step 5 | Repeat steps 2–4 for an additional 29 cycles   |
| Step 6 | 72° C. for 180 sec                             |
| Step 7 | 4° C. (and holding)                            |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN®, Boston, Mass.). The labeled oligonucleotides are substantially purified with Sephadex G-superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.).

Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, NY) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered.

This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the MT-MDH-encoding sequence, or any part thereof, is used to decrease or inhibit expression of naturally occurring MT-MDH. Although use of oligonucleotides comprising from about to about base-pairs is described, essentially the same procedure is used with smaller or larger sequence fragments. Appropriate oligonucleotides are designed using Oligo 4.06 software and the coding sequence of MT-MDH, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MT-MDH-encoding transcript.

IX Expression of MT-MDH

Expression of MT-MDH is accomplished by subcloning the cDNAs into appropriate vectors and transforming the vectors into host cells. In this case, the cloning vector is also used to express MT-MDH in *E. coli* . Upstream of the cloning site, this vector contains a promoter for β-galactosidase, followed by sequence containing the amino-terminal Met, and the subsequent seven residues of βgalactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of MT-MDH into the bacterial growth media which can be used directly in the following assay for activity.

X Demonstration of MT-MDH Activity

Malate dehydrogenase activity is assayed in a Beckman DU640i spectrophotometer at 340 nm with temperature controlled cuvette holders at 37° C. as described (Loeber, et al. (1994, supra)). The standard assay reaction mixture for the decarboxylation reaction contain 50 mM tris-HCl, pH 7.4, 3 mM $MnCl_2$, 5 mM malate, and 0.12 mM $NAD(P)^+$. Malate carboxylation reactions ('reverse reaction') are measured in 50 mM tris-HCl, pH 7.4, 50 mM pyruvate, 75 mM $KHCO_3$, 1 mM $MnCl_2$, 0.2 mM NAD(P)H. Changes in absorbance at 340 nm are measured continuously over a period of fifteen minutes.

XI Production of MT-MDH Specific Antibodies

MT-MDH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides 15 are residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring MT-MDH Using Specific Antibodies

Naturally occurring or recombinant MT-MDH is substantially purified by immunoaffinity chromatography using antibodies specific for MT-MDH. An immunoaffinity column is constructed by covalently coupling MT-MDH antibody to an activated chromatographic resin, such as CNBr-activated Sepharose (Pharmacia & Upjohn). After the coupling, the resin is blocked and washed according to the manufacturer's instructions.

Media containing MT-MDH is passed over the immunoaffinity column, and the column is washed under conditions that allow the preferential absorbance of MT-MDH (e.g., high ionic strength buffers in the presence of detergent). The column is eluted under conditions that disrupt antibody/MT-MDH binding (eg, a buffer of pH 2–3 or a high concentration of a chaotrope, such as urea or thiocyanate ion), and MT-MDH is collected.

XIII Identification of Molecules which Interact with MT-MDH

MT-MDH or biologically active fragments thereof are labeled with $^{125}I$ Bolton-Hunter reagent (Bolton et al. (1973) Biochem. J. 133: 529). Candidate molecules previously arrayed in the wells of a multi-well plate are incubated with the labeled MT-MDH, washed and any wells with labeled MT-MDH complex are assayed. Data obtained using different concentrations of MT-MDH are used to calculate values for the number, affinity, and association of MT-MDH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polypeptide selected from the group consisting of:
    a) a polypeptide comprising the amino acid sequence of SEQ ID NO:1, and
    b) a fragment of a polypeptide comprising the amino acid sequence of SEQ ID NO:1,
wherein said fragment has malate dehydrogenase activity.

2. The polypeptide of claim 1, having the amino acid sequence of SEQ ID NO:1.

3. A composition comprising the polypeptide of claim 1 and an excipient.

4. A method of screening a compound for effectiveness as an activator of a polypeptide of claim 1, the method comprising:

a) exposing a sample comprising a polypeptide of claim 1 to a compound, and
b) detecting, directly or indirectly, an increase of malate dehydrogenase activity.

5. A method of screening a compound for effectiveness as an inhibitor of a polypeptide of claim 1, the method comprising:

a) exposing a sample comprising a polypeptide of claim 1 to a compound, and
b) detecting directly or indirectly, an decrease of malate dehydrogenase activity.

* * * * *